United States Patent [19]

Abdallah et al.

[11] 4,150,133

[45] Apr. 17, 1979

[54] METHOD FOR TREATING DEPRESSION AND ANXIETY USING PHENYL HYDRAZO COMPOUNDS

[75] Inventors: Abdulmuniem H. Abdallah; Philip J. Shea, both of Midland, Mich.

[73] Assignee: The Dow Chemical Company, Midland, Mich.

[21] Appl. No.: 897,314

[22] Filed: Apr. 18, 1978

Related U.S. Application Data

[62] Division of Ser. No. 810,348, Jun. 27, 1977, Pat. No. 4,117,146.

[51] Int. Cl.$^2$ .......................................... A61K 31/505
[52] U.S. Cl. ................................................... 424/251
[58] Field of Search ........................................ 424/251

*Primary Examiner*—Stanley J. Friedman
*Attorney, Agent, or Firm*—James W. Ambrosius

[57] ABSTRACT

Methods and pharmaceutical compositions using substituted phenyl hydrazo compounds for the treatment of depression and/or anxiety in a mammal.

11 Claims, No Drawings

METHOD FOR TREATING DEPRESSION AND ANXIETY USING PHENYL HYDRAZO COMPOUNDS

CROSS REFERENCE TO RELATED APPLICATION

This is a division, of application Ser. No. 810,348 filed June 27, 1977, now U.S. Pat. No. 4,117,146.

BACKGROUND OF THE INVENTION

Halo-substituted phenylazoimidazoles are described at CA 72:111427a (Khim. Geterotsikl Soedin 916-22, 1969). Other substituted phenylazoimidazoles are shown in J. Chem. Soc., 115, 226 (1919) and in J. Chem. Soc., 117, 1426 (1920). None of the references cited disclose the use of the compounds to treat an animal.

U.S. Pat. No. 3,480,630 discloses the use of 2-arylhydrazino-imidazoline-(2) as a hypotensive in warm-blooded animals.

SUMMARY OF THE INVENTION

The present invention is directed to a method of treating depression and/or anxiety in a mammal using a compound of the formula

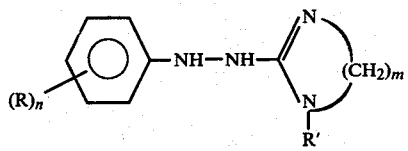

wherein R is chloro or fluoro; R' is hydrogen or methyl; n is the integer one or two; and m is the integer two or three whereby the resulting heterocyclic ring including the two nitrogen atoms is imidazole or pyrimidine.

The invention also includes the pharmaceutically-acceptable salts of the compounds used in the practice of the present invention. As used in the specification and claims, the term "pharmaceutically-acceptable salts" refers to non-toxic acid addition salts of the active compounds, the anions of which are relatively innocuous to animals at dosages consistent with good antidepressant and antianxiety activity so that the beneficial effects of the free base are not vitiated by the side effects ascribable to the anions. Pharmaceutically-acceptable salts include those derived from mineral acids such as hydrochloric and sulfuric and from organic acids such as lactic, maleic, succinic, fumaric, glutaric, citric, malic, p-toluenesulfonic, methanesulfonic, and tartaric acid and the like.

In general, the compounds used in the practice of the present invention are administered in daily dosages of from about 0.5 mg to about 100 mg of active ingredient per kilogram of body weight to relieve depression and/or anxiety in a mammal. The compounds are administered internally to a mammal either orally or parenterally by subcutaneous, intravenous or intraperitoneal injection or the like, oral administration being preferred. The effective psychoactive amount of the compounds of the invention to be administered internally to a mammal, that is the amount which is effective to substantially relieve a mammal of the symptoms of depression and/or anxiety, can vary depending upon such factors as the animal treated, the particular compound administered, the period of administration, and the method of administration.

DETAILED DESCRIPTION OF THE INVENTION

In practicing the method of the invention, one or more of the compounds described herein are administered internally to a mammal by a route that will introduce an effective psychoactive amount of the compound into the blood stream of the mammal. Administration can be carried out either by a parenteral route such as by intravenous, intraperitoneal, subcutaneous or intramuscular injection, or by introduction into the gastrointestinal tract by oral administration, for example, to introduce the compound into the blood via the gastrointestinal tract. The active compounds are orally effective, and generally have a higher ratio of toxic dose to effective dose when orally administered, and this route is preferred. The effective amount of the compounds to be administered can also be referred to as a "psychoactive amount" (amount sufficient to alleviate Central Nervous System depression and/or anxiety). Likewise, the terms antidepressant amount and antianxiety amount refers to the amount sufficient to alleviate Central Nervous System depression and anxiety, respectively.

The psychoactive amount of compound, that is, the amount of the active compound sufficient to provide the desired effect depends on various known factors such as the size, type, age and condition of the animal to be treated, the particular imidazole or pyrimidine, the pharmaceutically-acceptable salt employed, the route and frequency of administration, the type and degree of Central Nervous System condition involved, the time the compound is administered relative to prior and subsequent presentation of food and liquids, etc. In particular cases, the dosage to be administered can be ascertained by conventional range finding techniques, for example, by observing the effect produced at different dosage rates.

Generally, the compound is administered at a daily dosage rate of from about 0.5 to about 100 mg/kg of bodyweight with about 0.5 to about 45 being preferred. Higher dosage rates may be employed, for example, when the compound is administered orally in a timed release dosage form. In the case of mammals suffering from Central Nervous System depression and/or anxiety (exhibiting symptoms of depression and/or anxiety), administration of a psychoactive amount of the active compound is preferably repeated at predetermined intervals. It is generally desirable to administer the individual dosages at the lowest psychoactive amount which provides the desired continuity consonant with a convenient dosing schedule.

In practicing the method of the invention, the active ingredient is preferably incorporated in a composition comprising a pharmaceutical carrier and from about 0.001 to about 95 percent by weight of the compound or a pharmacologically-acceptable salt thereof. The term "pharmaceutical carrier" refers to known pharmaceutical excipients useful in formulating pharmacologically-active compounds for internal administration to animals, and which are substantially non-toxic and non-sensitizing under conditions of use.

Suitable pharmaceutical carriers are known and disclosed in texts such as Remington's Pharmaceutical Sciences, Thirteenth Ed., Martin (Ed.) Mack Publishing Co., Easton, Pa. (1965). The compositions can be prepared by known techniques for the preparation of tablets, capsules, lozenges, troches, elixirs, syrups, emulsions, dispersions, wettable and effervescent powders, and sterile injectable compositions, and can contain suitable excipients known to be useful in the preparation of the particular type of composition desired.

Dosage units adaptable to oral administration such as tablets, capsules, lozenges, elixirs, syrups and the like are preferred and the active compound can be formulated in conventional timed release capsule or tablet formulations.

Preferred compositions include sterile injectable solutions containing from about 0.001 to about 10 percent by weight of the active compound in a pharmaceutical carrier suitable for injection, such as isotonic saline solution, Ringer's Injection USP, and lactated Ringer's USP, and the like. Preferred compositions for oral use include unit dosage forms such as capsules and compressed tablets, containing a pharmaceutical carrier and from about 1 to about 150 milligrams of active compound per unit.

The following examples further illustrate the method that is the present invention.

EXAMPLE 1

Separate groups of mice of the same origin and past history (5 mice per group) were administered 2-(2-(2-chlorophenyl)hydrazino)-4,5-dihydro-1H-imidazole monohydrochloride in an aqueous carrier. Different groups were administered the compound by intraperitoneal injection at various dosage rates. Thirty minutes after the administration of the test compound, the mice were administered reserpine at a dosage rate of 2.5 milligrams per kilogram by intraperitoneal injection. Separate groups of similar mice were similarly administered 2.5 milligrams of reserpine per kilogram 30 minutes after administration of various dosages of the known antidepressant. The mice were then observed for 45 minutes for symptoms of reserpine-induced depression.

In repeated prior check observations, the administration of 2.5 milligrams per kilogram (mg/kg) of reserpine intraperitoneally to mice has been observed to result in a classical progression of symptoms beginning with a characteristic drooping of the eyelids (ptosis) and later culminating in a generalized depression with decreased spontaneous motor activity and decreased responsiveness to auditory and tactile stimuli. Protection from reserpine-induced depression is indicated by the absence of the characteristic ptosis.

The results were employed to calculate the dose effective to protect 50 percent of the mice ($ED_{50}$) by classical, statistical procedures. The imidazole salt was found to have an $ED_{50}$ of less than 10 mg/kg. In other operations, the intraperitoneal acute 50 percent lethal dose ($LD_{50}$) was found to be 167 mg/kg.

EXAMPLE 2

The procedure of Example 1 was repeated using oral administration of 2-(2-(2-chlorophenyl)hydrazino)-4,5-dihydro-1H-imidazole monohydrochloride instead of intraperitoneal injection. The oral $ED_{50}$ was found to be 2 mg/kg of body weight.

Using the general procedure outlined above, the $ED_{50}$'s were calculated for other compounds showing antidepressant properties. These compounds are represented by the general formula

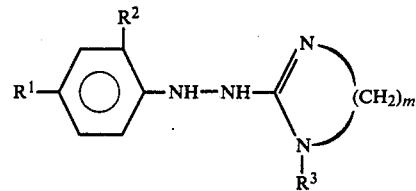

The results are shown in Table I below.

TABLE 1

| Compound Ex. No. | $R^1$ | $R^2$ | $R^3$ | m | Salt | ORAL $ED_{50}$ mg/kg | Intraperitoneal $ED_{50}$ mg/kg |
|---|---|---|---|---|---|---|---|
| 3 | H | F | H | 2 | HCl | 1.0 | less than 10 |
| 4 | H | F | CH$_3$ | 2 | no | 27 | 37 |
| 5 | H | F | H | 3 | HCl | 43 | 37 |
| 6 | Cl | Cl | CH$_3$ | 2 | HI | — | 43 |

The data indicate the compounds 2-(2-(2-chlorophenyl)hydrazino)-4,5-dihydro-1H-imidazole monohydrochloride and 2-((2-fluorophenyl)hydrazino)-4,5-dihydro-1H-imidazole monohydriodide (Example 3) are particularly active as antidepressants and as such are preferred.

The following compounds were also found to be active as antidepressants. The mean effective dose was not calculated for these compounds.

2-(2-(2-chlorophenyl)hydrazino)-1,4,5,6-tetrahydropyrimidine monohydriode.

2-(2-(4-chlorophenyl)hydrazino)-4,5-dihydro-1-methyl-1H-imidazole monohydriodide.

2-(2-(2,4-dichlorophenyl)hydrazino)-1,4,5,6-tetrahydro-1-methylpyrimidine monohydriodide.

2-(2-(2,4-dichlorophenyl)hydrazino)-1,4,5,6-tetrahydropyrimidine monohydriodide.

EXAMPLE 7

Antianxiety agents tend to block isolation-induced aggression in mice. Aggression was established in untrained mice by isolating them in individual cages for a period of four weeks. At the end of that period, the mice were paired for three minutes on three test days within one week to establish the absence or presence of aggression. During pairing, one mouse was always in the home cage, and the other was the intruder. If the pair of mice fought at least two of three test sessions, they were used for antianxiety demonstration.

On test days, each dose of test drug was administered by intraperitoneal injection to five pairs of mice; five additional pairs received only the vehicle and served as controls. Each drug was tested at three doses 10.0 mg, 21.5 mg, and 46.4 mg per kilogram of body weight. Thirty minutes after injection, the intruder was placed in the home cage of his opponent, and aggression was recorded as absent or present. When aggression was present, the intruder was removed immediately so that dominance was not established.

Using the method described in Example 7, the following compounds were found to possess antianxiety activity.

2-(2-(2-chlorophenyl)hydrazino)-4,5-dihydro-1H-imidazole monohydrochloride.

2-(2-(2-chlorophenyl)hydrazino)-1,4,5,6-tetrahydropyrimidine monohydriode.

2-((2-fluorophenyl)hydrazino)-4,5-dihydro-1H-imidazole monohydriode.

2-(2-(4-chlorophenyl)hydrazino)-4,5-dihydro-1-methyl-1H-imidazole monohydriodide.

2-(2-(2,4-dichlorophenyl)hydrazino)-1,4,5,6-tetrahydro-1-methylpyrimidine monohydriodide.

2-(2-(2,4-dichlorophenyl)hydrazino)-1,4,5,6-tetrahydropyrimidine monohydriodide.

It will be noted that several compounds display both antidepressant activity and antianxiety activity. The compounds 2-(2-(2-chlorophenyl)hydrazino)-4,5-dihydro-1H-imidazole monohydrochloride and 2-((2-fluorophenyl)hydrazino)-4,5-dihydro-1H-imidazole monohydriodide are particularly preferred for this reason.

What is claimed is:

1. A method for alleviating symptoms of Central Nervous System depression and anxiety in a mammal which comprises administering internally to said mammal a psychoactive amount of a compound or a pharmaceutically-acceptable salt thereof having the formula

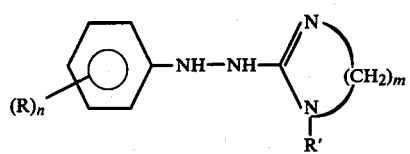

wherein R is chloro or fluoro; R' is hydrogen or methyl; n is the integer one or two; and m is the integer three whereby the resulting heterocyclic ring including the two nitrogen atoms is pyrimidine.

2. The method of claim 1 wherein the compound or a pharmaceutically-acceptable salt thereof is administered in combination with a pharmaceutically-acceptable carrier.

3. A method for alleviating symptoms of Central Nervous System depression in a mammal which comprises administering internally to said mammal an antidepressant amount of a compound or a pharmaceutically-acceptable salt thereof having the formula

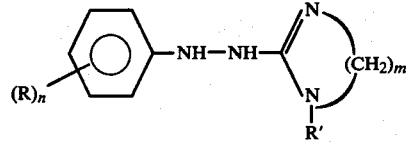

wherein R is chloro or fluoro; R' is hydrogen or methyl; n is the integer one or two; and m is the integer three whereby the resulting heterocyclic ring including the two nitrogen atoms is pyrimidine.

4. The method of claim 3 wherein the compound or a pharmaceutically-acceptable salt is administered in combination with a pharmaceutically-acceptable carrier.

5. The method of claim 3 wherein the compound is 2-(2-(2-fluorophenyl)hydrazino)-1,4,5,6-tetrahydropyrimidine or a pharmaceutically-acceptable salt thereof.

6. The method of claim 3 wherein the compound is 2-(2-(2-fluorophenyl)hydrazino)-1,4,5,6-tetrahydro-1-methylpyrimidine or a pharmaceutically-acceptable salt thereof.

7. A method for alleviating symptoms of Central Nervous System anxiety in a mammal which comprises administering internally to said mammal an antianxiety amount of a compound or a pharmaceutically-acceptable salt thereof having the formula

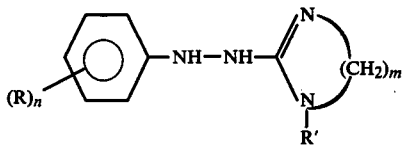

wherein R is chloro or fluoro; R' is hydrogen or methyl; n is the integer one or two; and m is the integer three whereby the resulting heterocyclic ring including the two nitrogen atoms is pyrimidine.

8. The method of claim 7 wherein the compound or a pharmaceutically-acceptable salt is administered in combination with a pharmaceutically-acceptable carrier.

9. The method of claim 7 wherein the compound is 2-(2-(2-chlorophenyl)hydrazino)-1,4,5,6-tetrahydropyrimidine or a pharmaceutically-acceptable salt thereof.

10. The method of claim 7 wherein the compound is 2-(2-(2,4-dichlorophenyl)hydrazino)-1,4,5,6-tetrahydro-1-methylpyrimidine or a pharmaceutically-acceptable salt thereof.

11. The method of claim 7 wherein the compound is 2-(2-(2,4-dichlorophenyl)hydrazino)-1,4,5,6-tetrahydropyrimidine or a pharmaceutically-acceptable salt thereof.

* * * * *